United States Patent [19]

Heinze

[11] Patent Number: 5,133,349
[45] Date of Patent: Jul. 28, 1992

[54] METHOD FOR ADAPTING THE STIMULATION FREQUENCY OF A HEART PACEMAKER TO THE BURDEN OF THE PATIENT

[75] Inventor: Roland Heinze, München, Fed. Rep. of Germany

[73] Assignee: Siemens Aktiengesellschaft, München, Fed. Rep. of Germany

[21] Appl. No.: 573,032
[22] PCT Filed: Feb. 6, 1989
[86] PCT No.: PCT/EP89/00108
 § 371 Date: Aug. 6, 1990
 § 102(e) Date: Aug. 6, 1990
[87] PCT Pub. No.: WO89/06990
 PCT Pub. Date: Aug. 10, 1989

[30] Foreign Application Priority Data
 Feb. 5, 1988 [DE] Fed. Rep. of Germany ....... 3803473

[51] Int. Cl.$^5$ ............................................. A61N 1/365
[52] U.S. Cl. ............................................. 128/419 PG
[58] Field of Search ............................. 128/419 PG

[56] References Cited

U.S. PATENT DOCUMENTS

| | | | |
|---|---|---|---|
| 4,202,339 | 5/1980 | Wirtzfeld et al. | 128/419 PG |
| 4,399,820 | 8/1983 | Wirtzfeld et al. | 128/419 PG |
| 4,702,253 | 10/1987 | Nsappholz et al. | 128/419 G |
| 4,763,655 | 8/1988 | Wirtzfeld et al. | 128/419 PG |
| 4,779,618 | 10/1988 | Mund et al. | 128/419 PG |
| 4,823,797 | 4/1989 | Heinze et al. | 128/419 PG |
| 4,827,933 | 5/1989 | Konig et al. | 128/419 PG |
| 4,830,488 | 5/1989 | Heinze et al. | 128/419 PG |
| 4,870,967 | 10/1989 | Heinze et al. | 128/419 PG |
| 4,903,701 | 2/1990 | Moore et al. | 128/419 PG |
| 4,919,137 | 4/1990 | Schaldach | 128/419 PG |

FOREIGN PATENT DOCUMENTS 0165566 12/1985 European Pat. Off.

Primary Examiner—William E. Kamm
Attorney, Agent, or Firm—Hill, Van Santen, Steadman & Simpson

[57] ABSTRACT

During optimization intervals prescribed by the heart pacemaker, the stimulation frequency is periodically changed and an acquisition of a measured value that is dependent on the cardiac minute output is respectively phase-synchronized with the change in stimulation frequency. An identification is thereby made whether the measured value that is dependent on the cardiac minute output changes given the change of the stimulation frequency. A number of curves are stored representing different relationships between a regulating variable, derived from the measured value, and the stimulation frequency. The stimulation frequency of the pacemaker is set based on one of these curves, as selected by an optimization controller to which the regulating variable is supplied. If the change in the measured valued as acquired during the optimization intervals indicates that the currently-selected curve is no longer accurate, the optimization controller selects another curve from among the stored curves which best represents the current relationship between the regulating variable and the stimulation frequency.

13 Claims, 4 Drawing Sheets

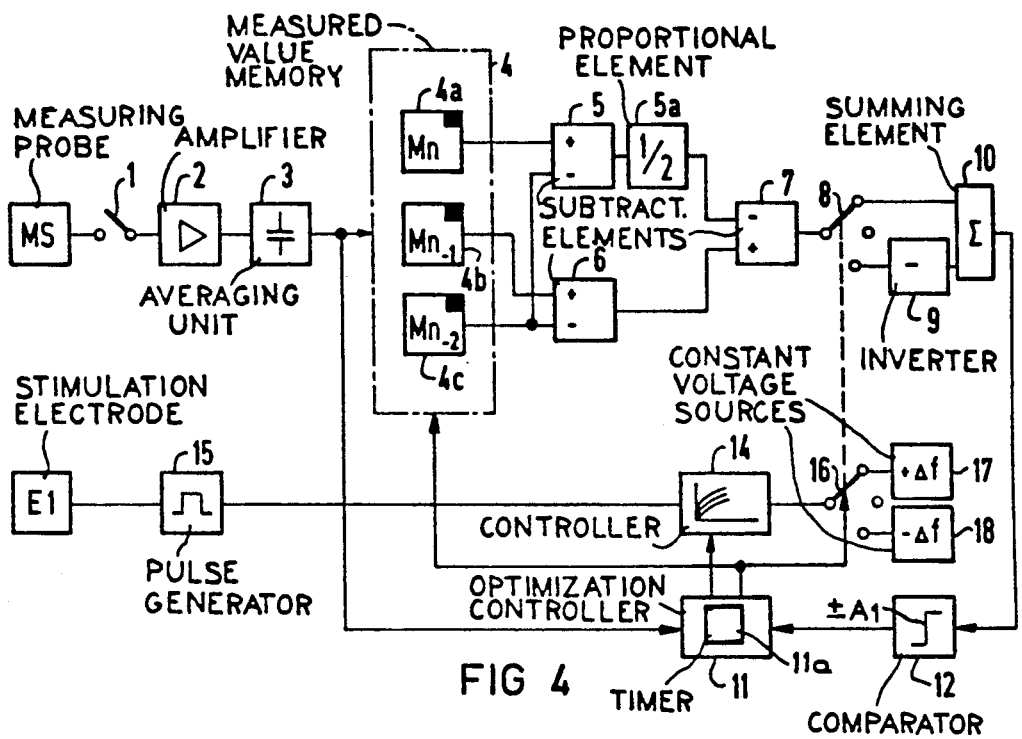
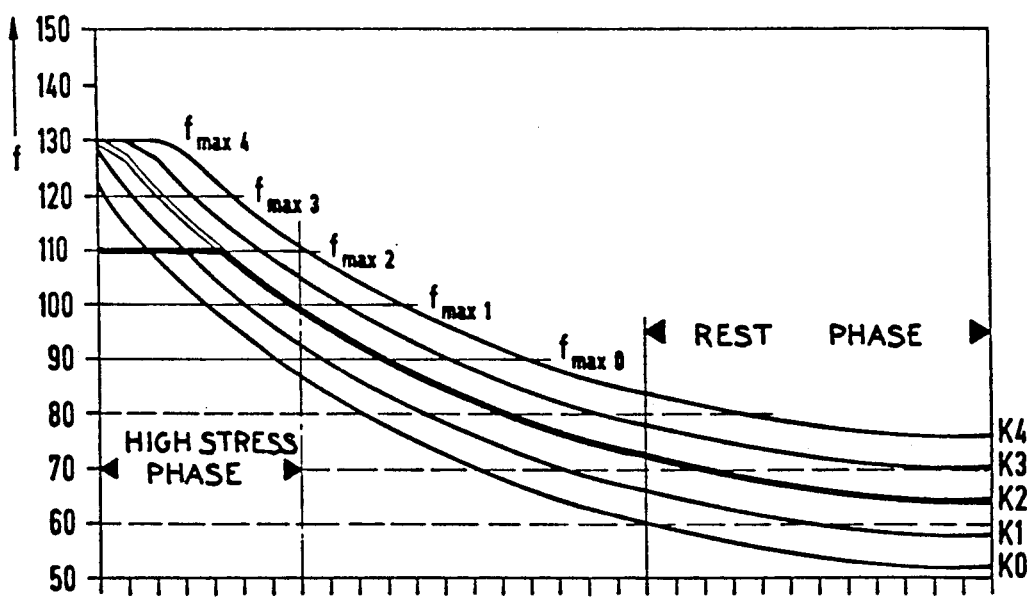

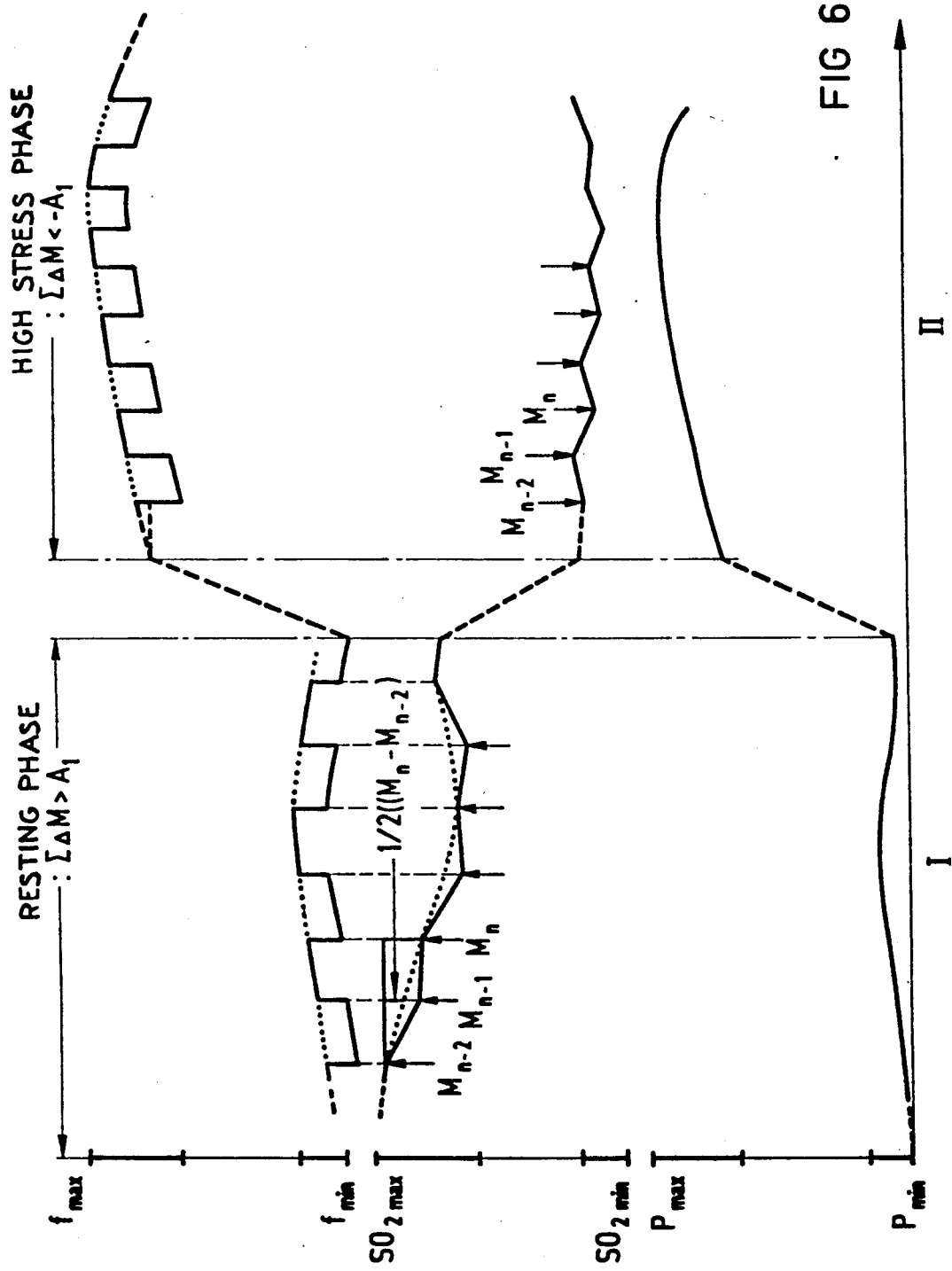

METHOD FOR ADAPTING THE STIMULATION FREQUENCY OF A HEART PACEMAKER TO THE BURDEN OF THE PATIENT

BACKGROUND OF THE INVENTION

1. Field of the Invention

The invention is directed to a method for adapting the stimulation frequency of a heart pacemaker to the burden of a patient, whereby a characteristics regulator controls the stimulation frequency dependent on a burden-dependent regulating variable and whereby, by changing the stimulation frequency during defined time intervals, an identification is made to see whether a measured value dependent on the cardiac minute output thereby changes, and whereby an optimization controller influences a characteristic that represents the relationship between the regulating variable and the stimulation frequency which correspondingly influences this change in measured value.

2. Description of the Prior Art

A method of this species is disclosed by EP-A-2 0 165 566. The stimulation frequency of a heart pacemaker is thereby regulated dependent on the central venous blood oxygen saturation in the heart. The central venous blood oxygen saturation is calculated according to the principle of reflection oximetry that, for example, is disclosed in detail in DE-A-31 52 963.

An optimum adaptation to the individual hemodynamic situation of the patient that changes over time is not possible with a permanently prescribed, invariable characteristic such as the relationship between blood oxygen saturation and stimulation frequency. In the EP-A2-0 165 566, an optimizing control that acts continuously in addition to the characteristics control is thereby provided. The optimizing control continuously monitors the tendency of the value of the blood oxygen saturation and, by automatic elevation or lowering of the frequency, determines whether an improvement (measured value increase) of the value of the blood oxygen saturation ensues or not. It is not only one defined characteristic but an entire family of characteristics that is now allocated to every value of blood oxygen saturation.

This arrangement, however, has the disadvantage that it makes a decision after every change in frequency whether a positive or negative reaction of the blood oxygen saturation ensued and, thus, there is the risk of incorrect decision as a consequence of disturbing changes of the oxygen saturation that are dependent on burden above all.

SUMMARY OF THE INVENTION

It is therefore an object of the present invention to design a method of the species initially cited such that the optimum adaptation of the regulation of the stimulation frequency to the hemodynamic situation of the patient becomes more independent o disturbing influences and is thus further improved.

This object is inventively achieved in that the change of the stimulation frequency is periodically repeated during optimization intervals prescribed by the heart pacemaker and an acquisition of the measured value dependent on cardiac minute output respectively ensues phase-synchronized with the change in stimulation frequency. Disturbing influences can be largely eliminated due to the multiple repetition of changes in the stimulation frequency.

DESCRIPTION OF THE DRAWINGS

FIG. 4 is a schematic block diagram of a control circuit for practicing the method of the present invention.

FIG. 5 is a graph showing a family of characteristic curves for oxygen saturation versus stimulation frequency in accordance with the principles of the present invention.

FIG. 6 shows a stimulation phase diagram for illustrating the principles of the method in accordance with the principles of the present invention.

DESCRIPTION OF THE PREFERRED EMBODIMENT

Figure 1:
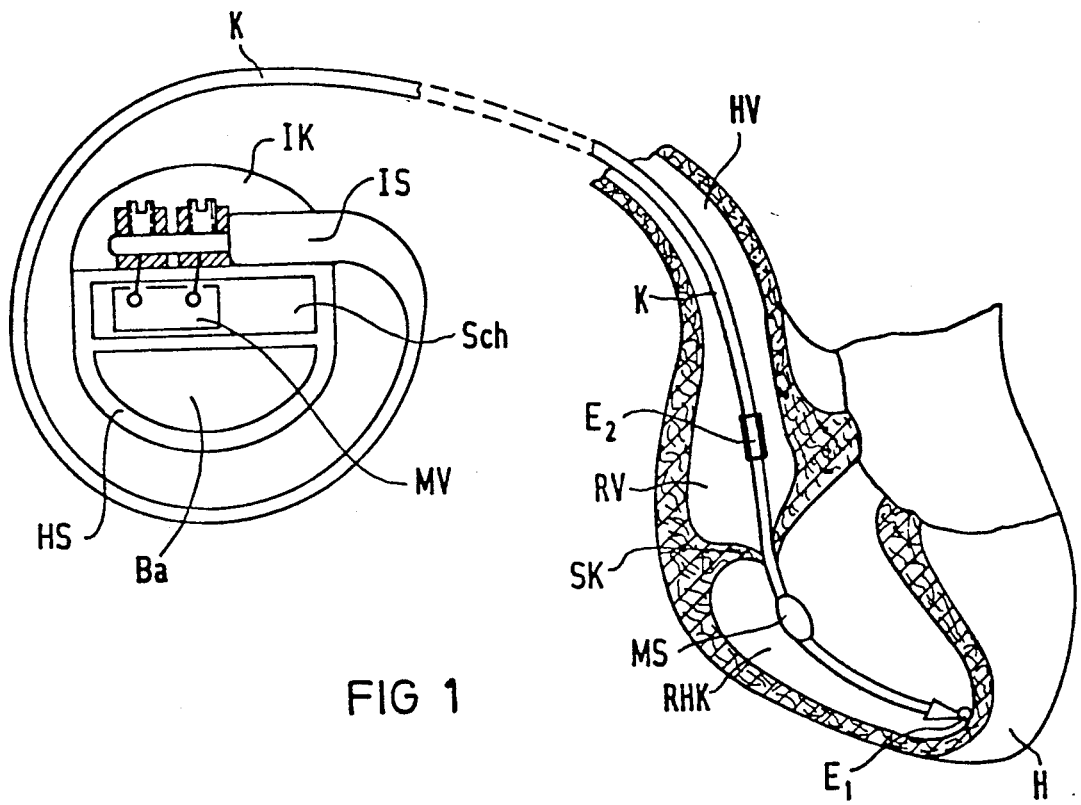
FIG. 1 generally shows a heart pacemaker and lead in relation to a human heart.

FIG. 1 shows an arrangement of a heart pacemaker known from DE-A-31 52 963. The heart pacemaker HS contains a power supply part Ba, an electronic switch Sch having a measuring amplifier MV, and the two-pole electrical coupling IK. The two-pole electrical plug IS of the stimulation catheter K is screwed fast in the coupling IK. Via the upper hollow vein HV, the stimulation catheter K leads into the right auricle RV in which the neutral sensing electrode $E_2$ is positioned and then leads into the right ventricle RHK. In the region of the right ventricle RHK, the stimulation catheter K contains a measuring probe MS that measures the blood oxygen saturation according to the principle of reflection oximetry. The cardiac muscle H is stimulated by the stimulation electrode $E_1$, whereby the stimulation frequency is dependent on the measured signal of the measuring probe MS, i.e. on the blood oxygen saturation. The blood oxygen saturation thus acts as a regulating quantity for the control of the stimulation frequency.

In the ideal case, the heart pacemaker should set the stimulation frequency such that the venous blood oxygen saturation is optimally high at an optimally low frequency given a constant physical exertion. This objective derives from the fact that the physiological adaptation of the cardiac muscle to physical exertions P is optimum when the cardiac minute output HMV is proportional to the physical exertion P: $HMV \hat{=} P$. In order to optimize the burden of the cardiac muscle, a defined cardiac minute output with optimally high stroke volume $SV_{max}$ should be achieved given optimally low pulse frequency $f_{bmin}$, i.e.

$$HMV_{opt}(P=\text{constant}) = SV_{max} \cdot f_{pmin}$$

It is also true that given a constant physical exertion (P=constant), i.e. given a constant oxygen drain of the blood in the peripheral circulation, the change of the venous blood oxygen $\Delta SO_2$ is proportional to the change of the cardiac minute output $\Delta HMV$. On the basis of the aforementioned relationships, the heart pacemaker—on the basis of an optimum value regulation—should select the characteristic curve from a family of characteristic curves which relate the cardiac minute volume (or a variable derived therefrom) to the—stimulation frequency that is best adapted to the efficiency of the cardiac muscle.

Figure 2:
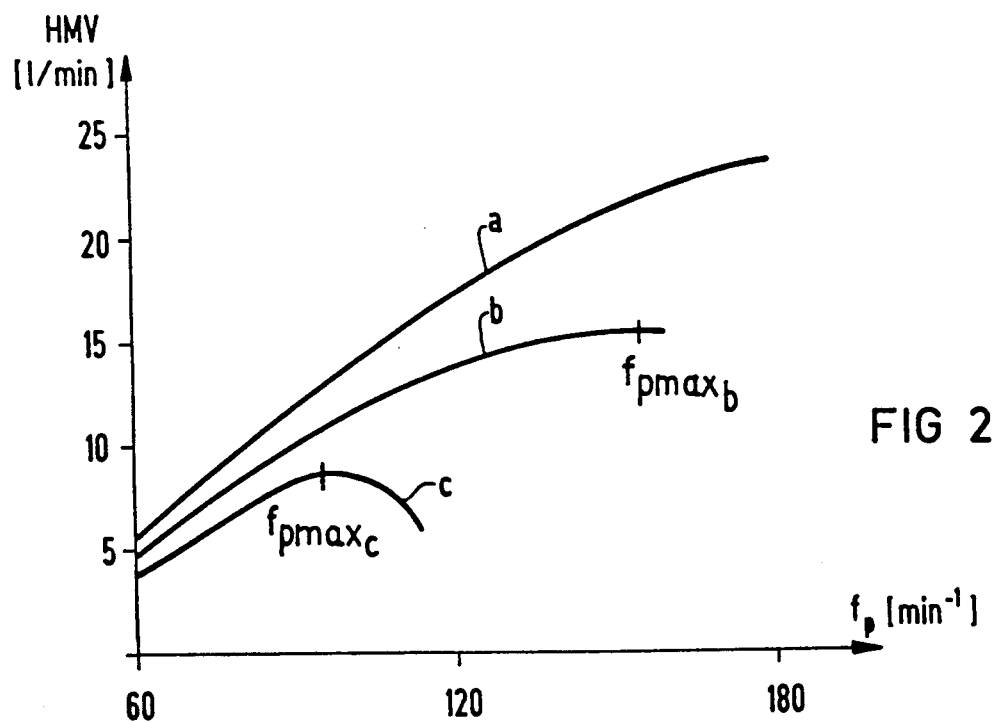
FIG. 2 is a graph showing the relationship between stimulation frequency and cardiac minute output.

FIG. 2 shows the relationship between the heart rate $f_p$ and the cardiac minute output HMV for a healthy myocardium (a) and for two cases of a diseased myocardium (curves b, c). One can see from the curves that the cardiac minute output HMV in the low load region increases approximately proportionally to the heart rate fp and, dependent on the efficiency of the myocardium, asymptotically reaches a limit value $HMV_{max}$. Characteristic of the diseased myocardium is the drop of the cardiac minute output HMV beginning with a maximum heart rate $f_{pmax}$, for which reason a heart rate above $f_{pmax}$ as stimulation frequency is to be avoided in all cases.

Figure 3:
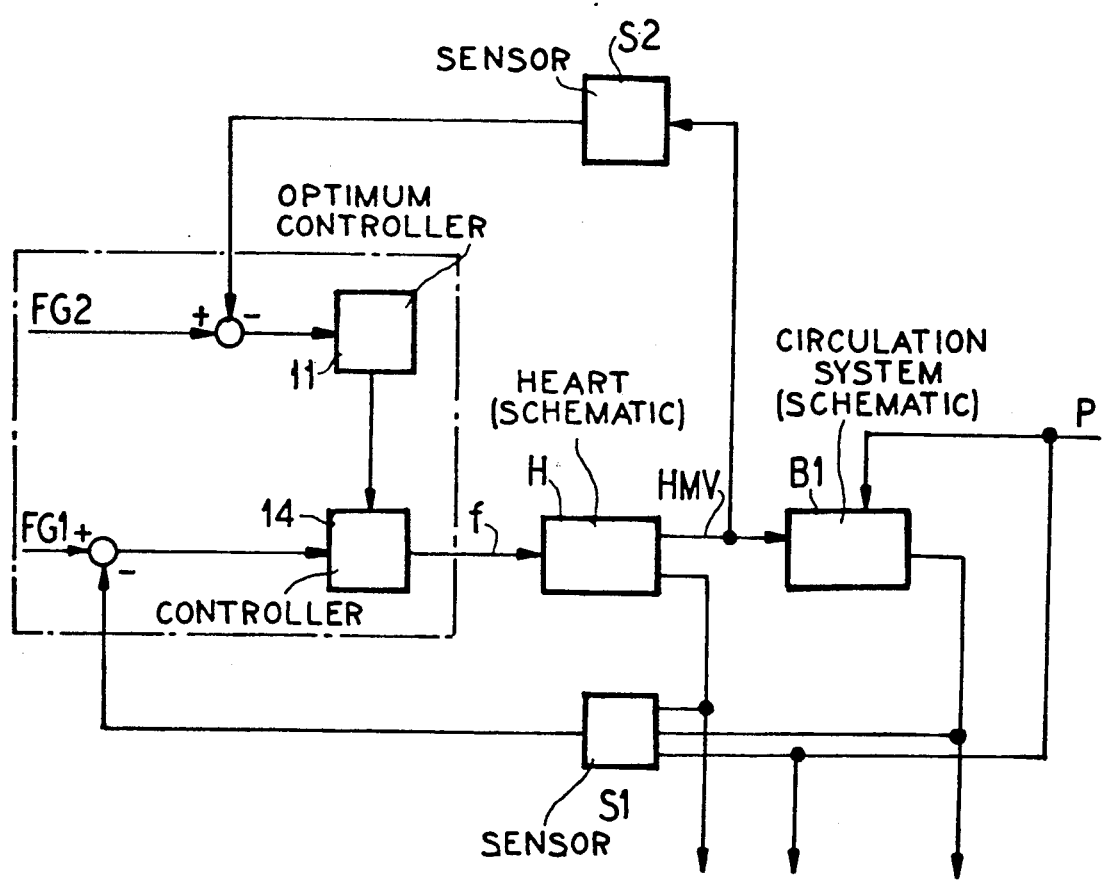
FIG. 3 is a schematic block diagram of the control path used in the method of the present invention.

FIG. 3 shows a control circuit for a physiological regulation of the stimulation frequency. The heart H is thereby to be considered as a control element that acts on the blood circulation BL via the cardiac minute output HMV. The blood circulation BL is also influenced by the physical exertion P that is to be considered as a disturbing quantity.

A first sensor S1 is provided for the acquisition of a burden-dependent physiological quantity, for example EKG, blood pressure, respiratory volume, or of a measured activity value of the physical exertion. Dependent on the required physiological quantity, the sensor S1 is interactively connected for this purpose to the heart H, to the blood circulation BL or to a quantity (P) that represents the physical exertion P, for example, the activity. Via a substraction element whose second input is supplied with a first reference variable input FG1, a regulating variable is formed from the output signal of the sensor S1, this regulating variable prescribing the stimulation frequency f for the heart H via the controller 14.

As a regulating signal, an optimization controller 11 receives the cardiac minute output HMV acquired via a second sensor S2, this being subtracted from a second reference variable input FG2. The sensor S2, for example, can thereby work according to the principle of impedance measurement. The optimization controller 11 regulates the relationship between the regulating variable and stimulation frequency prescribed by the controller 14 to an optimum value.

As shown in FIG. 4 another possibility for optimum regulation uses only one measuring probe MS for the blood oxygen saturation $SO_2$. The measured value of the blood oxygen saturation $SO_2$ is thereby supplied both to the controller 14 as well as to the optimization controller 11, being supplied thereto as the regulating variable. The sensors S1 and S2 are eliminated. In the embodiment of FIG. 3, FG1 is a reference variable for the first physiological quantity provided by sensor S1, and FG2 is a reference variable for the second physiological quantity provided by sensor S2. In the embodiment of FIG. 4, the selection of a curve corresponds to the reference variable FG2, and the curve itself corresponds to FG1.

The measuring probe MS is thereby connected to a measured value memory 4 via a switch 1, a measuring amplifier 2 and an averaging unit 3. The measured value memory 4 contains memories 4a–4c for the respectively current measured value $M_n$ and two respectively preceding measured values $M_{n-1}$ and $M_{n-2}$.

Two subtraction elements 5 and 6 follow the measured value memory 4, whereby the subtraction element 5 subtracts the measured value $M_{n-2}$ from the measured value $M_n$ and the subtraction element 6 subtracts the measured value $M_{n-2}$ from the measured value $M_{n-1}$. The output of the subtraction element 5 is connected via a proportional element 5a having the proportional factor $\frac{1}{2}$ to the minus input of a further subtraction element 7 and the subtraction element 6 is connected to the plus input of the subtraction element 7. Via a switch 8, the subtraction element 7 is optionally connectible directly to the input of a summing element 10 for the measured values obtained in an optimization phase (yet to be set forth), via an inverter 9 to the same summing element 10 or to a free contact. The switch 8 is driven by an optimization controller 11 acting as an optimum regulator. The output of the summing element 10 is connected via a comparator 12 to an input of the optimization controller 11. Further, the optimization controller 11 is controlled by the measured value taken at the output of the averaging unit 3. The optimization controller 11 acts on a controller 14 having a curve generator. Dependent on the value curve prescribed by the optimization controller 11, the controller 14 regulates the frequency f of a pulse generator 15 that is connected to the stimulation electrode E1.

The functioning of the control circuit shall be set forth in greater detail below with reference to FIGS. 5 and 6.

FIG. 5 shows a family of curves for the relationship between the normed blood oxygen saturation $SO_{2norm}$ and the stimulation frequency f. The blood oxygen saturation $SO_2$ is acquired with the measuring probe MS, is amplified with the measured value amplifier 2, is averaged with the averaging unit 3 and is normed in the optimization controller 11. The curves K0–K4 are stored in the curve generator of the controller 14, whereby switching to different curves can be undertaken based on a signal from optimization controller 11.

Further, five maximum values $f_{max0}$–$f_{max4}$ for the stimulation frequency are defined. The maximum values $f_{max0}$–$f_{max4}$ are defined by the optimization controller 11. Each curve K0–K4 can be cut by one of the maximum values $f_{max0}$–$f_{max4}$. A curve K that is best adapted to the efficiency of the cardiac muscle is to be selected with the optimum regulation from the family of characteristics shown in FIG. 5.

To this end, two characteristic, physical conditions or phases are first defined wherein an individual adaptation of the stimulation frequency is particularly important, namely, in the resting phase and in the high-stress phase. Both phases are shown in FIG. 5.

In the "resting phase", the physical activity acquired by a region of high, normed oxygen saturation $SO_2$ is reduced to a minimum. A low oxygen drain is present and the central venous value of the oxygen saturation reaches its maximum.

In the "high-stress phase", the physical performance acquired by a range of low, normed oxygen saturation $SO_{2norm}$ reaches an individually typical, maximum quantity, i.e. a maximum oxygen drain is present given a minimum central venous value of the oxygen saturation $SO_2$.

It should be noted that the terms "in phase" and "phase-synchronized" as used herein have their normally understood wave mechanics meaning of two signals having the same phase angle or phase angles differing by a fixed amount. These terms do not refer to the above "resting phase" or "high-stress phase".

Ideal conditions for an optimizing frequency adaptation would be established if a central venous oxygen saturation $SO_2$ in the range between 70 and 80%, i.e. a value as in the case of a person with a healthy heart, were to be achieved and if a cardiac minute output that is maximum for the patient could be set in the high-stress phase.

The prerequisite for such an optimization, however, would be an absolute measurement value of the oxygen and of the stroke volume. These measured quantities, however, cannot be directly acquired with existing methods. A measuring method wherein the measured quantities are indirectly acquired is therefore used for the optimum regulation.

The optimization method employed is fundamentally based, due to the periodic change of the stimulation frequency and the in-phase measured value calculation, on the acquisition of data identifying as to whether and how the frequency change influences the hemodynamic situation, i.e. the cardiac minute output of the patient. Since the cardiac minute output cannot be directly acquired, the oxygen saturation $SO_2$ dependent on the cardiac minute output is employed as an equivalent quantity.

Insofar as the optimization circuit is activated, optimization intervals are carried out at regular intervals of, for example, six hours initiated by a timer $11a$ in the optimization controller 11. An optimization is thereby carried out only during the resting phase and during the high-stress phase. The sequence of an optimization shall be set forth in greater detail below with reference to the diagram of FIG. 6.

FIG. 6 shows an assumed burden curve P of the patient for an optimization interval I (resting phase) and for an optimization interval II (high-stress phase) that lies a number of hours later. The stimulation frequency f that derives on the basis of a preselected curve K is shown with dotted lines over the burden P. Further, the curve of the oxygen saturation SO, is shown, whereby the dotted line again represents the curve deriving without optimum regulation. The optimization in the resting phase I starts with a lowering of the stimulation frequency f, namely, by, for example, eight beats per minute in the resting phase. This lowering of the frequency lasts, for example, 48 heartbeats and is subsequently cancelled for 48 heartbeats and is then repeated. In order to suppress brief-duration disturbing influences—for instance, due to burden fluctuations—16 frequency changes, for example, are executed per optimization interval and disturbing influences are then eliminated by formation of an average signal, or a combination of signals over them, according to known methods.

As the pulse diagram of FIG. 6 shows, a measured value $M_n$ of the oxygen saturation $SO_2$ is stored synchronously with every frequency change. The measured values $M_n$ are measured with a time delay (hysteresis) of four beats in order to take the delay of the blood stream in the venous circulation into consideration.

Two preceding measured values $M_{n-1}$ and $M_{n-2}$ are stored in the measured value memory 4 for every measured value $M_n$.

The calculation of the measured values $\Delta M$ ensues after every change period, i.e., for example, after 96 heartbeats, whereby the measured value difference $\Delta M_n$ that is determined is defined according to the following equation:

$$\Delta M = (M_{n-1} - M_{n-2}) - \tfrac{1}{2}(M_n - M_{n-2}) \text{ given}$$
elevation of stimulation frequency $$\Delta M = -(M_{n-1} - M_{n-2}) + \tfrac{1}{2}(M_n - M_{n-2}) \text{ given}$$
lowering of stimulation frequency If the difference between two successive measured values were simply employed, then the influence of burden changes that yield the dotted curve of the oxygen saturation $SO_2$ would thus also have been acquired. However, only the influence of the frequency change is to be identified. When it is assumed that the curve of the oxygen saturation $SO_2$ is linear without the periodic change in stimulation frequency, then a change of the oxygen saturation of $\tfrac{1}{2}(M_n - M_{n-2})$ that is independent of the periodic frequency change is obtained at the measured value $M_{n-1}$. When, given an elevation of the stimulation frequency, this factor $\tfrac{1}{2}(M_n - M_{n-2})$ is subtracted from the overall measured value change $(M_n - M_{n-2})$ or, respectively, this value is added given a lowering of the stimulation frequency f, then the change $\Delta M$ of the measured value for the oxygen saturation caused by the periodic change of the stimulation frequency is obtained with a good approximation.

As already mentioned, 16 difference measurements, for example, are preferably executed in succession, whereby only one part of the frequency change is shown in FIG. 6 for the sake of clarity. A combination of all 16 measured value changes $\Delta M$ is then utilized for the optimization regulation.

For example, a correlation function known from Profos, Handbuch der industriellen Messtechnik, 1978, Pages 185 through 189 could thereby be utilized. In the described exemplary embodiment, however, the sum $\Sigma \Delta M$ of the measured value changes is evaluated in that the measured values $\Delta M$ pending at the output of the summing element 7 are supplied to the summing element 10.

In the sum formation of the measured value changes $\Delta M$, of course, the measured value changes $\Delta M$ obtained during frequency lowerings must be evaluated with the inverse operational sign compared to the measured value change $\Delta M$ obtained given frequency elevations, this ensuing with the inverter 9.

The calculation of the measured value changes in a high-stress phase is implemented in analogous fashion during an optimization interval II. In the high-stress phase, the change of the stimulation frequency with, for example, 16 per minute can be selected higher than in the resting phase. A measured value change $\Delta M$ employed for the optimization regulation is also obtained in the high-stress phase by sum formation after 16 different measurements.

It is possible that the provided number of measured value changes $\Delta M$, 16 in the example, cannot be acquired in a respective optimization cycle I II because, for example, the burden P of the patient has changed in the meantime. In this case, the measured value changes $\Delta M$ that are already acquired are stored and are used for the next optimization cycle.

The measured value $\Sigma \Delta M$ pending at the output of the summing element 10 after the implementation of the measured value acquisition addressed above are now compared to two thresholds $-A_1$ and $+A_1$ in the comparator 12. Dependent on the result of the comparison, the optimum curve is selected from the family of curve of FIG. 5 in accordance with the table on page 13. In the resting phase, it is thereby only the curve K that is defined, whereas the maximum stimulation frequency $f_{max}$ is determined in the high-stress phase. When it is assumed that the characteristic 2 shown emphasized in FIG. 5 was first set in the curves generator of the controller 14 and the maximum stimulation frequency $f_{max2}$ was set, then, for example, it is thus the curve K1 that is selected when the sum of the measured value changes $\Sigma\Delta M$ in at least one optimization interval is $<A_1$, i.e. when an improvement of the oxygen saturation was thus achieved by reducing the stimulation frequency f. By contrast, the curve K3 is selected when the sum of the measured value changes in an optimization interval I, i.e. in the resting phase, is $>-A_1$. This means that an improvement of the oxygen saturation $SO_2$ was achieved by elevating the stimulation frequency, so that the curves K3 seems better-suited for the patient.

When the sum of the measured value changes lies between $-A_1$ and $+A_1$ in an optimization interval I in the resting phase, it can be concluded that a change of the stimulation frequency has no significant influence on the blood oxygen saturation $SO_2$. The curve K2 is thus initially retained. When, however, the sum of the measured value changes $\Sigma\Delta M$ in two successive optimization intervals I lies between $-A_1$ and $+A_1$, the characteristic K1 is activated. This derives from the efforts to always give lower stimulation frequencies precedence in doubtful cases since the cardiac muscle is thereby treated more gently. If a deterioration of the oxygen saturation were to result from the switch to the curve K1, then the sum of the measured value changes $\Sigma\Delta N$ will again be $>-A_1$ in the next optimization interval I and the curve K2 will thus be again selected.

When, however, the characteristic K0, i.e. the lower limit curve, is activated and the sum of the measured value changes $\Sigma\Delta M$ lies between $-A_1$ and $+A_1$ in two successive optimization intervals I, a switch to curve K1 is undertaken. This prevents the optimization regulation from getting stuck at the lower limit curve K0.

Analogous measures according to the illustrated table are also implemented in the case of an optimization interval II for the high-stress phase. The only difference that exists is that it is not the curves K per se that are thereby influenced, but the limit value $f_{max}$ for the stimulation frequency f.

Various values for the resting phase and for the high-stress phase can be prescribed for the constants A1 and A2 dependent on the sensitivity of the measuring probe MS and on the hemodynamic reserve of the patient.

from a succession of said measured values, and selecting a characteristic that best represents the relationship between the regulating variable and stimulation frequency in accord with this measured value change from among a plurality of stored characteristics respectively representing different relationships between the regulating variable and stimulation frequency, the improvement comprising the steps of identifying a series of chronologically spaced optimization intervals, periodically changing the stimulation frequency during each optimization interval, acquiring a series of said measured values dependent on the cardiac minute output respectively at times which are phase-synchronized with the change in stimulation frequency, and updating the selection of said characteristic that best represents the relationship between the regulating variable and stimulation frequency using said measured values acquired during said optimization interval.

2. The improvement of claim 1, comprising the additional steps of obtaining a correlation value identifying a correlation between all measured values that are acquired during a frequency change period and measured values of the preceding frequency change periods; and setting the characteristics burden-dependent regulating variable-stimulation frequency based on said correlation value.

3. The improvement of claim 1, comprising the additional steps of calculating the measured value changes obtained during an optimization interval, and selecting the characteristic representing the relationship between regulating variable and stimulation frequency based on the calculation.

4. The improvement of claim 3, comprising the additional step of comparing the calculation of the measured value changes in an optimization interval to an upper, positive limit value and to a lower, negative limit value, and wherein the step of selecting the characteristic representing the relation between regulating variable and stimulation frequency is defined by the steps of:
a) shifting the characteristic toward lower stimulation frequencies when the calculation of the measured value changes is less than $-A1$ in at least one optimization interval;
b) maintaining the characteristic unaltered when the calculation of the measured value changes lies between $-A1$ and $+A1$; and

| Combination | Condition | Set Characteristic or, respectively, limit frequency | Change Given Resting Phase | High-Stress Phase |
|---|---|---|---|---|
| 1 | 1 time $< A_1$ | 1–4 | Lower to the next curve (K0–K3) | Lower the limit frequency by one step ($f_{max}\,0$–$f_{max}\,3$) |
| 2 | 1 time $< A_1$ and $> -A_1$ | 0–4 | Curve Remains | Limit frequency remains |
| 3 | 2 time $< A_1$ and $> -A_1$ | 1–4 | Lower to next curve (K0–K3) | Lower limit frequency by one step ($f_{max}\,0$–$f_{max}\,3$) |
| 4 | 2 time $< A_1$ and $> -A_1$ | 0 | Increased to next curve (K1) | Increase limit frequency by one step ($f_{max}\,1$) |
| 5 | 1 time $> -A_1$ | 0–3 | Increase to curve (K1–K4) | Increase limit frequency by one step ($f_{max}\,a$–$f_{max}\,4$) |

I claim as my invention:

1. In a method for adapting the stimulation frequency of a heart pacemaker to the burden of a patient, including the steps of acquiring a measured value dependent on the cardiac minute output, changing the stimulation frequency during defined time intervals dependent on whether said measured value dependent on the cardiac minute volume changes, deriving a regulating variable c) shifting the characteristic in the direction of higher stimulation frequencies when the calculation of the measured value changes is greater than A1 in at least one optimization interval.

5. The improvement of claim 4, wherein the step (a) is further defined as shifting the characteristic in the direction of lower stimulation frequencies when the calculation of the measured value changes lies between $-A1$ and $A1$ in two successive optimization intervals.

6. The improvement of claim 4, wherein step (c) is further defined as shifting the characteristic in the direction of higher stimulation frequencies when the calculation of the measured value changes in two successive optimization intervals lies between $-A1$ and $A1$ and a lower limit characteristic is reached.

7. The improvement of claim 6 wherein said optimization intervals include a resting phase and a high stress phase, and comprising the additional steps of conducting steps (a), (b) and (c) only during said rest phase.

8. The improvement of claim 3, wherein said stimulation frequency has an upper limit $f_{max}$, wherein said optimization intervals include a high stress phase, and comprising the additional steps of comparing the calculation of the measured value changes to an upper, positive limit value $A1$ and to a lower, negative limit value $-A1$ and varying the upper limit $f_{max}$ according to the following steps during a high stress phase of the patient;
   a) reducing the limit value $f_{max}$ when the calculation of the measured value changes $\Delta M$ in at least one optimization interval is less than $-A1$ and the upper limit $f_{max}$ has not yet reached a lowest prescribed value;
   b) maintaining the upper limit $f_{max}$ unaltered when the calculation of the measured value changes $\Delta M$ lies between $-A1$ and $+A1$; and
   c) increasing the upper limit value $f_{max}$ when the calculation of the measured value changes $\Delta M$ in at least one optimization interval is greater than $A1$ and the upper limit $f_{max}$ has not yet reached an uppermost, prescribed value.

9. The improvement of claim 8, wherein step (a) is further defined by reducing the upper limit $f_{max}$ when the calculation of the measured value changes $\Delta M$ lies between $-A1$ and $A1$ in two successive optimization intervals and the upper limit $f_{max}$ has not yet reached said lowest, prescribed value.

10. The improvement of 8, the upper limit value $f_{max}$ when the calculation of the measured value changes lies between $-A1$ and $A1$ in two successive optimization intervals and the upper limit $f_{max}$ has reached said lowest, prescribed value.

11. The improvement of claim 1, comprising the additional steps of storing, for each current measured value $Mn$, at least two measured values $M_{n-1}$ and $M_{n-2}$ acquired in preceding stimulation frequency changes, and calculating a measured value change $\Delta M$ according to one of the following equations:

$$\Delta M = (M_{n-1} - M_{n-2}) - \tfrac{1}{2}(M_n - M_{n-2}), \text{ and}$$

given a decrease of the stimulation frequency $$\Delta M = -(M_{n-1} - M_{n-2}) = \tfrac{1}{2}(M_n - M_{n-2}).$$

12. The improvement of claim 1 comprising the additional steps of determining whether each stimulation frequency change is positive or negative, assigning a positive value to a measured value change occurring as a result of a positive stimulation frequency change, and assigning a negative value to a measured value change occurring as a result of a negative stimulation frequency change.

13. The improvement of claim 1, comprising the additional step of, if a number of measured value changes adequate for an optimization procedure cannot be acquired in a current optimization interval, storing and re-using the measured value changes from a preceding optimization interval as measured value changes in said current optimization interval.

* * * * *